US007905232B2

(12) United States Patent
Olsen et al.

(10) Patent No.: US 7,905,232 B2
(45) Date of Patent: Mar. 15, 2011

(54) BREATHING ASSISTANCE APPARATUS

(75) Inventors: Gregory James Olsen, Auckland (NZ);
Martin Leckie, Auckland (NZ); Neil Prime, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 10/242,903

(22) Filed: Sep. 13, 2002

(65) Prior Publication Data
US 2003/0047185 A1 Mar. 13, 2003

(30) Foreign Application Priority Data

Sep. 13, 2001 (NZ) ..................................... 514184

(51) Int. Cl.
*A61G 10/00* (2006.01)
*A61M 16/00* (2006.01)
*A62B 18/02* (2006.01)
*A62B 18/08* (2006.01)
*A62B 9/02* (2006.01)

(52) U.S. Cl. ......... 128/207.18; 128/206.11; 128/206.28; 128/207.11; 128/207.13; 128/207.16

(58) Field of Classification Search ............. 128/207.18, 128/207.16, 207.17, 206.18, 205.25, 201.13, 128/203.18, 203.22, 204.11, 204.12, 204.18, 128/204.26, 206.21, 207.11, 207.13, 206.28, 128/206.11, 857, 858, DIG. 23
See application file for complete search history.

(56) References Cited

U.S. PATENT DOCUMENTS

| 1,081,745 | A |   | 12/1913 | Johnston et al. |
| 1,356,708 | A |   | 10/1920 | Goodyear |
| 1,443,820 | A |   | 1/1923  | Hudson |
| 1,873,160 | A |   | 8/1932  | Sturtevant |
| 2,295,321 | A | * | 9/1942  | Anderson ............... 128/206.18 |
| 2,383,649 | A |   | 8/1945  | Heidbrink |
| 2,414,405 | A | * | 1/1947  | Bierman et al. ......... 128/201.19 |
| 2,444,417 | A |   | 7/1948  | Bierman |
| 2,675,803 | A |   | 4/1954  | Kaslow |

(Continued)

FOREIGN PATENT DOCUMENTS

DE 29902267 9/1999

(Continued)

OTHER PUBLICATIONS

Gumnar Moa, MD; Kjell Nilsson, MD; Henrik Zetterstrom, MD, PHD; Lars O. Jonsson MD, PHD., "A New Device for Administration of Nasal Continous Positive Airway Pressure in the Newborn: An Experimental Study", Critical Care Medical, pp. 1238-1242, vol. 16 No. 12, Copyright: Dec. 1988 by Williams & Wilkins Co.

*Primary Examiner* — Patricia M Bianco
*Assistant Examiner* — Brandon Jackson
(74) *Attorney, Agent, or Firm* — Knobbe, Martens, Olson & Bear, LLP

(57) ABSTRACT

A nasal cannula for delivering respiratory gas to a neonatal infant includes a gas inlet configured to engage a respiratory conduit, a gas outlet configured to engage an expiratory conduit, and a pair of nasal prongs. The gases inlet and the gases outlet are in fluid communication via a low resistance path. Each of the nasal prongs is located substantially equidistant from, and in fluid communication with, the gases inlet, and substantially equidistant from and in fluid communication with, the gases outlet. The nasal prongs are juxtaposed directly in the low resistance path.

10 Claims, 10 Drawing Sheets

U.S. PATENT DOCUMENTS

| | | |
|---|---|---|
| 2,765,792 A | 10/1956 | Nichols |
| 2,837,090 A | 8/1958 | Bloom et al. |
| 3,013,556 A | 12/1961 | Galleher, Jr. |
| 3,065,747 A | 11/1962 | Forkel |
| 3,079,917 A | 3/1963 | Pate |
| 3,513,844 A | 5/1970 | Smith |
| 3,643,660 A | 2/1972 | Hudson et al. |
| 3,792,702 A | 2/1974 | Delest |
| 3,910,269 A | 10/1975 | Ansite et al. |
| 3,987,798 A | 10/1976 | McGinnis |
| 4,002,167 A | 1/1977 | Rambosek |
| 4,106,505 A * | 8/1978 | Salter et al. ............... 128/207.18 |
| 4,120,300 A | 10/1978 | Tiep |
| 4,151,843 A * | 5/1979 | Brekke et al. ............ 128/205.25 |
| 4,216,769 A * | 8/1980 | Grimes .................... 128/207.13 |
| D257,449 S * | 10/1980 | Johnson, Jr. .................... D2/889 |
| 4,235,229 A | 11/1980 | Ranford et al. |
| 4,367,735 A | 1/1983 | Dali |
| 4,414,973 A | 11/1983 | Matheson et al. |
| 4,459,983 A | 7/1984 | Beyreuther et al. |
| 4,572,177 A * | 2/1986 | Tiep et al. ................ 128/205.17 |
| 4,641,647 A * | 2/1987 | Behan ...................... 128/207.18 |
| 4,732,147 A | 3/1988 | Fuller |
| 4,739,755 A | 4/1988 | White et al. |
| 4,774,946 A * | 10/1988 | Ackerman et al. ....... 128/207.18 |
| 4,785,832 A | 11/1988 | Gherardi et al. |
| 4,823,789 A | 4/1989 | Beisang, III |
| 4,832,019 A * | 5/1989 | Weinstein et al. ........ 128/207.17 |
| 4,907,584 A | 3/1990 | McGinnis |
| 4,919,128 A * | 4/1990 | Kopala et al. ............ 128/207.18 |
| 5,003,632 A | 4/1991 | Claude |
| 5,038,776 A | 8/1991 | Harrison et al. |
| 5,042,477 A | 8/1991 | Lewis |
| 5,042,478 A * | 8/1991 | Kopala et al. ............ 128/207.18 |
| 5,069,206 A | 12/1991 | Crosbie |
| 5,074,229 A * | 12/1991 | Sasako et al. .............. 112/102.5 |
| 5,074,295 A | 12/1991 | Willis |
| 5,097,827 A | 3/1992 | Izumi |
| 5,113,857 A * | 5/1992 | Dickerman et al. ...... 128/207.18 |
| 5,117,818 A * | 6/1992 | Palfy ........................ 128/204.11 |
| 5,123,410 A | 6/1992 | Greene et al. |
| 5,137,017 A * | 8/1992 | Salter ........................ 128/207.18 |
| 5,146,913 A | 9/1992 | Khorsandian et al. |
| 5,156,641 A | 10/1992 | White |
| 5,181,507 A | 1/1993 | Michel et al. |
| 5,193,532 A * | 3/1993 | Moa et al. ................ 128/204.25 |
| 5,237,986 A | 8/1993 | Seppala et al. |
| 5,243,971 A | 9/1993 | Sullivan et al. |
| 5,251,616 A | 10/1993 | Desch |
| 5,271,391 A * | 12/1993 | Graves ..................... 128/207.18 |
| 5,282,463 A | 2/1994 | Hammersley |
| 5,335,656 A * | 8/1994 | Bowe et al. .............. 128/207.18 |
| 5,375,593 A | 12/1994 | Press |
| 5,383,451 A | 1/1995 | DeIulio |
| 5,438,979 A * | 8/1995 | Johnson et al. .......... 128/207.18 |
| 5,477,852 A | 12/1995 | Landis et al. |
| 5,513,635 A | 5/1996 | Bedi |
| 5,533,506 A * | 7/1996 | Wood ....................... 128/207.18 |
| 5,537,997 A | 7/1996 | Mechlenburg et al. |
| 5,542,128 A | 8/1996 | Lomas |
| 5,570,689 A | 11/1996 | Starr et al. |
| 5,613,502 A * | 3/1997 | Lee .............................. 128/857 |
| 5,645,058 A * | 7/1997 | Odom ...................... 128/207.18 |
| 5,653,228 A | 8/1997 | Byrd |
| 5,662,101 A | 9/1997 | Ogden et al. |
| 5,682,881 A | 11/1997 | Winthrop et al. |
| 5,687,715 A * | 11/1997 | Landis et al. ............ 128/207.18 |
| 5,735,272 A | 4/1998 | Dillon et al. |
| 5,752,510 A | 5/1998 | Goldstein |
| 5,832,918 A | 11/1998 | Pantino |
| 5,921,239 A | 7/1999 | McCall et al. |
| 5,975,077 A * | 11/1999 | Hofstetter et al. ........ 128/204.24 |
| 5,975,079 A | 11/1999 | Hellings et al. |
| 6,019,101 A * | 2/2000 | Cotner et al. ............ 128/207.13 |
| 6,044,844 A | 4/2000 | Kwok et al. |
| 6,047,699 A | 4/2000 | Ryatt et al. |
| 6,067,985 A * | 5/2000 | Islava ...................... 128/207.17 |
| 6,192,886 B1 | 2/2001 | Rudolph |
| 6,338,342 B1 | 1/2002 | Fecteau et al. |
| 6,374,826 B1 | 4/2002 | Gunaratnam et al. |
| 6,439,234 B1 * | 8/2002 | Curti et al. ............... 128/207.18 |
| 6,457,473 B1 | 10/2002 | Brostrom et al. |
| 6,470,886 B1 * | 10/2002 | Jestrabek-Hart ......... 128/207.11 |
| 6,494,207 B1 | 12/2002 | Kwok |
| 6,520,182 B1 | 2/2003 | Gunaratnam |
| 6,536,435 B1 | 3/2003 | Fecteau et al. |
| 6,536,436 B1 * | 3/2003 | McGlothen ............. 128/207.18 |
| 6,591,837 B1 | 7/2003 | Byram |
| 6,612,309 B1 | 9/2003 | Ancona |
| 6,615,834 B2 | 9/2003 | Gradon et al. |
| 6,691,708 B2 | 2/2004 | Kwok et al. |
| 6,701,926 B2 | 3/2004 | Olsen et al. |
| 6,715,490 B2 | 4/2004 | Byram |
| 6,789,541 B2 * | 9/2004 | Olsen et al. .............. 128/207.11 |
| 6,796,308 B2 | 9/2004 | Gunaratnam et al. |
| 6,823,869 B2 | 11/2004 | Raje et al. |
| 6,840,238 B1 | 1/2005 | Van Hegelsom |
| D540,463 S * | 4/2007 | Aylsworth et al. ........ D24/110.1 |
| 7,578,294 B2 * | 8/2009 | Pierro et al. ............. 128/207.13 |
| 2002/0005201 A1 * | 1/2002 | Gradon et al. ........... 128/207.11 |
| 2003/0000533 A1 * | 1/2003 | Olsen et al. .............. 128/206.21 |
| 2003/0111080 A1 | 6/2003 | Olsen et al. |
| 2003/0127094 A1 * | 7/2003 | Roberts ..................... 128/203.22 |
| 2003/0200970 A1 * | 10/2003 | Stenzler et al. .......... 128/207.18 |
| 2004/0112377 A1 | 6/2004 | Amarasinghe et al. |
| 2004/0244804 A1 | 12/2004 | Olsen et al. |
| 2005/0056286 A1 | 3/2005 | Huddart et al. |
| 2007/0186931 A1 * | 8/2007 | Zollinger et al. ........ 128/207.11 |

FOREIGN PATENT DOCUMENTS

| | | |
|---|---|---|
| EP | 549299 | 6/1993 |
| EP | 1084727 | 3/2001 |
| EP | 1084727 A2 * | 3/2001 |
| WO | WO 9848876 | 11/1998 |
| WO | WO 0189381 | 11/2001 |

* cited by examiner

BREATHING ASSISTANCE APPARATUS

FIELD OF INVENTION

This invention relates to Nasal Cannulae particularly though not solely to nasal cannulae for delivering Continuous Positive Airway Pressure (CPAP) to neonates.

BACKGROUND

Certain individuals require a respiratory supplement such as air, oxygen, or other gases. Such gases are freely supplied and/or supplied at controlled pressures. Such gases are also supplied through the patient's mouth and/or through the patient's nose. Nasal supply systems provide an advantage in that they are generally more convenient and less intrusive than mouth based or mouth covering devices. Despite their convenience, nasal based devices are deemed uncomfortable in light of securement straps placed across the face and/or around the head and used to secure the device to an individuals breathing cavity. Moreover, conventional cannulas do not provide a proper seal around the nares to inhibit apnea and to provide a high flow system to stimulate the patient's breathing. Hence, even with such securement straps, these nasal devices often dislodge from the breathing cavity. This is of particular concern with children, infants, or the elderly who do not understand the importance of keeping the nasal breathing device in place, whether it be a nasal CPAP or nasal cannula.

It is known to be beneficial and therapeutic to supply an individual with a sufficient amount of respiratory airway pressure in order to maintain a minimum level of air volume in the lungs. If the air volume falls below this minimum level, then the lungs may collapse, which can be extremely dangerous or even deadly to the individual. Moreover, the back pressure can increase oxygen levels in the lungs and decrease carbon dioxide levels. This will also improve PH by removal of carbon dioxide, which is an acid, from the blood. Hence, the application of such sufficient pressure, called continuous positive airway pressure (CPAP), has been found to be advantageous in maintaining a minimum air volume or lung pressure when an individual is spontaneously breathing. CPAP can be supplied through nasal attachment devices such as a nasal cannulae, or through mouth based or endotracheal devices.

A number of CPAP devices are known including endotracheal tubes, head chambers, face chambers, face masks, nasal prongs, and nasal cannula. While each type of device has advantages and disadvantages, the nasal cannula provides a comfortable alternative for providing CPAP and/or airflow assistance. Prior art nasal cannulae have been disclosed in many forms with various methods of securing the device to the nasal passageway. One such cannula assembly is disclosed in U.S. Pat. No. 3,513,844 which uses an adjustable strap that encircles an individual's head. A similar device is disclosed in U.S. Pat. No. 4,106,505 wherein the supply tubes to the cannula are hooked over an individual's ears and around the head. Even more cumbersome, U.S. Pat. No. 5,477,852 discloses a device with a headband for holding and positioning the nasal inserts and associated supply tubes. Yet another system in U.S. Pat. No. 5,271,391 discloses a cannula which is secured by applying strips of pressure sensitive adhesive tape to the supply tubes leading from each side of the cannula, thereby attaching the supply tubes to the cheeks of an individual with the cannula positioned in between.

"Bonnet" type devices are also used to hold the CPAP nasal cannulae in place. However, this method generally puts pressure on an individual's nose and upper lip thereby causing pressure necrosis in the centre of the nose. A particularly sensitive individual is a young child, infant or baby. The bonnet also fails to adequately keep the nasal prongs in position, particularly with infants who move or roll around in their crib. In a hospital or care facility setting, it is not uncommon for an attendant to discover that the CPAP device has been disconnected from a patient's nose, which can lead to apnea, desaturations, bradycardia, or hypoxia which is dangerously low oxygen levels in the blood. In practice, the tubing for these bonnet type CPAP's is draped around both sides of the patient's cheek which means that the most comfortable lying down position is on the patient's back. Pressure on the patient's cheeks caused by the securement device can make other positions uncomfortable.

Other prior art anchoring systems include adhesive devices which attach directly to the nose. U.S. Pat. No. 4,823,789 discloses a nose tube anchoring strip which has an adhesive coated sheet shaped to fit over an individual's nose and an appendage for holding a nasal-gastric tube. A similar system is found in U.S. Pat. No. 5,156,641 which has an anchoring cord adhesively attached to an individual's nose at one end and attached to hold a naso-gastric catheter at the other end. U.S. Pat. No. 5,513,635 provides a securement device with a body engagement portion which adheres across the nose of an individual with cannula engaging portions extending down therefrom. Similarly, U.S. Pat. No. 5,682,881 discloses the use of an adhesive foam pad secured to the upper lip for positioning of the cannula.

In U.S. Pat. No. 3,643,660 a unified nasal cannula comprises a hollow tubular body having an upper flat or plane surface and a pair of spaced and curved elongated tubular extensions, having exterior orifices for directing a gas flow which extensions project upwardly at an angle from the surface. Referring to FIGS. 2 and 3 we see that because the inlet 400 is from one side the prongs 402,404 may see slightly different pressures. There is also the potential for downstream prong 404 to rebreathe the expired $CO_2$ from upstream prong 402.

In U.S. Pat. No. 5,975,077 a cannula is disclosed including an airway injecting gas in fluid communication with nostrils of a patient and aerodynamically designed passageways for both the ambient air and the injected gas to optimize the fluid flow characteristics during inhalation and exhalation of the patient.

In U.S. Pat. No. 4,774,946 a cannula is described attached to an elongated flexible tube. The nasal prongs include bulbous portions that seat and seal the nasal tubes in the nares.

In U.S. Pat. No. 5,193,532 a device is disclosed for generating by ejector action a continuous positive airway pressure (CPAP), comprising a breathing-channel which at one end opens into the atmosphere and at another end is adapted to be provided with an attachment device to the nose and/or mouth of the patient as seen in FIG. 1. The inlet is situated between a channel open to the atmosphere and open to the prongs in such a manner that the stream of fresh gas is directed mainly co-axially into the channel, producing an ejector action.

However, while these prior art systems do provide nasal CPAP they suffer from a number of disadvantages including: insufficiently securement to the patients head, potential for unbalanced pressure in each prong, and potential for rebreathing of expired $CO_2$.

SUMMARY OF THE INVENTION

It is an object of the present invention to provide a nasal cannula which goes someway to overcoming the above mentioned disadvantages or which will at least give the public a useful choice.

Accordingly in a first aspect the present invention consists in a nasal cannula for delivering respiratory gas to a neonatal infant comprising:

a gases inlet configured to engage an inspiratory conduit,
a gases outlet configured to engage an expiratory conduit,
a hollow manifold chamber, said gases inlet and said gases outlet in fluid communication through said chamber,
a pair of nasal prongs, each of said prongs substantially equidistant from, and in fluid communication with, said gases inlet through said manifold chamber and substantially equidistant from and in fluid communication with said gases outlet through said manifold chamber,
said hollow manifold chamber providing a low resistance path between said gases inlet and said gases outlet and configured internally to limit the deadspace of said nasal cannula substantially to the volume of said prongs, said prongs juxtaposed directly in said low resistance path.

In a further aspect the invention consists in a system for delivering respiratory gas to a patient comprising a source of pressurised gas,
an inhalatory conduit in fluid communication with said source of gas and adapted to convey gas,
a nasal cannula in fluid communication with said inhalatory conduit and adapted to deliver gas to the nasal passages of an infant,
an exhalatory conduit in fluid communication with said cannula and adapted to convey gas from said cannula,
a pressure regulating device disposed within or in fluid communication with said exhalatory conduit and adapted to achieve a predetermined mean pressure of gas delivered to the nasal passages of a neonatal infant by regulating the flow of gas through said exhalatory conduit,
said nasal cannula including a low resistance path between said inhalatory conduit and said exhalatory conduit.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the forgoing and also envisages constructions of which the following gives examples.

BRIEF DESCRIPTION OF THE DRAWINGS

One preferred form of the present invention will now be described with reference to the accompanying drawings in which.

DETAILED DESCRIPTION OF THE PREFERRED EMBODIMENTS

Figure 11:
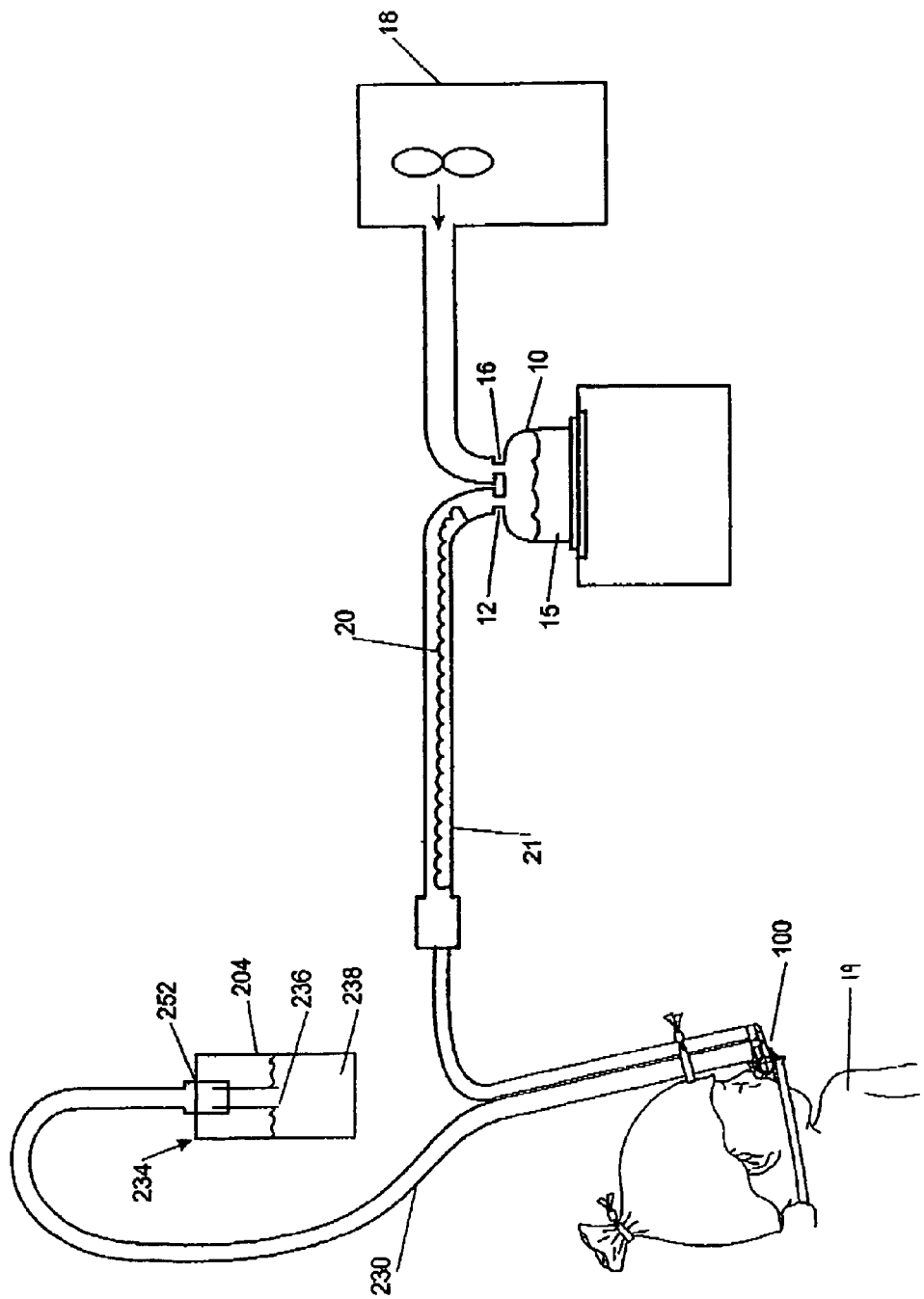
FIG. 11 is a block diagram of a CPAP system, in use with the present invention.

Referring now to FIG. 11 in which a typical application is depicted. A humidified Continuous Positive Airway Pressure (CRAP) system is shown in which a patient 19 is receiving humidified and pressurised gases through a nasal cannula 100 connected to a inhalatory conduit 21. It should be understood that the present invention, however, is not limited to the delivery of CPAP gases but is also applicable to other types of gases delivery systems. Inhalatory conduit 21 is connected to the outlet 12 of a humidification chamber 10 which contains a volume of water 15. Inspiratory conduit 21 may contain heating means or heater wires 20 which heat the walls of the conduit to ensure a constant humidity profile along the conduit and therefore reduce condensation of humidified gases within the conduit. As the volume of water 15 within humidification chamber 10 is heated, water vapour begins to fill the volume of the chamber above the water's surface and is passed out of the humidification chamber 10 outlet 12 with the flow of gases (for example air) provided from a gases supply means or blower 18 which enters the chamber 10 through inlet 16.

Figure 5:
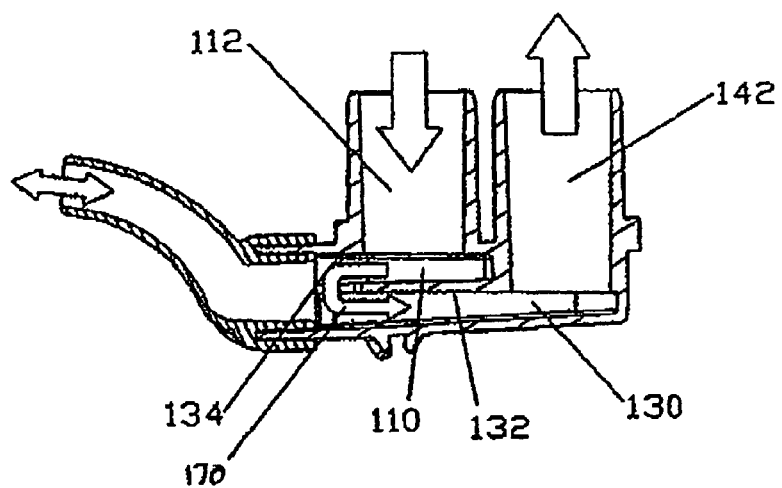
FIG. 5 is a section view of the present invention.

With reference to FIGS. 5 and 11, the humidified gases pass through the inhalatory conduit 21 to the cannula 100, which is in communication with the nose of a patient 19 through prongs 116,118. The expired gases pass through the prongs 116,118 to the output manifold 130. The excess gases then flow through the exhalatory conduit 230. It is preferred that exhalatory conduit 230 is connected to a pressure regulator 234.

In the preferred embodiment of the present invention the flow of exhalatory gases is discharged into a chamber 204 containing a column of water 238, as seen in FIG. 11. The gases flowing through the exhalatory conduit 230 are discharged into the body of water 238 from a short conduit 236 which extends from the expiratory conduit into the vessel 204. This results in a bubbling effect, whereby the gases eventually exit the vessel 204 via the outlet port 252, which can also be used to initially fill the chamber 204 with water. The outlet port 252 includes shielding to prevents liquid aerosols created by the vigorous bubbling on the surface of the water from being expelled. It will be appreciated that the short conduit 236, could equally be integrated into the end of the expiratory conduit 230. It will also be appreciated that by adjusting the level of which the short conduit 236 is submerged in the body of water 238 the mean pressure of supplied gases through the cannula 100 can be controlled.

Nasal Cannula

Referring now to FIGS. 4 to 10 the nasal cannula 100 is seen in more detail. The inlet manifold 110, is connected to an inlet port 112. Inlet port 112 accepts the gas flow from the humidifier and air/oxygen blender or any other flow source apparatus as would be appropriate. The diameter of the inlet manifold 110 is as large as possible to ensure minimal pressure drop in the gases before delivery to the patient. In fluid communication with the inlet manifold are two nasal prongs 116, 118. The gases are then able to flow from the inlet manifold 110 up through the nasal prongs into the corresponding nares of the patient. The prongs 116, 118 themselves are cylindrical with a slight taper narrowing at the top. The diameter is carefully chosen such that it will substantially seal against the interior of the nare, without imparting any substantial pressure thereon. As well as sealing this also provides some level of securement and keeps the cannula 100 in place.

Figure 4:
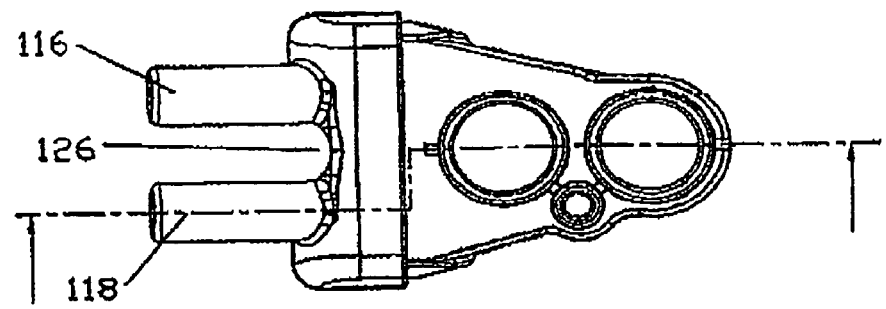
FIG. 4 is a perspective view from above of the present invention.
Figure 6:
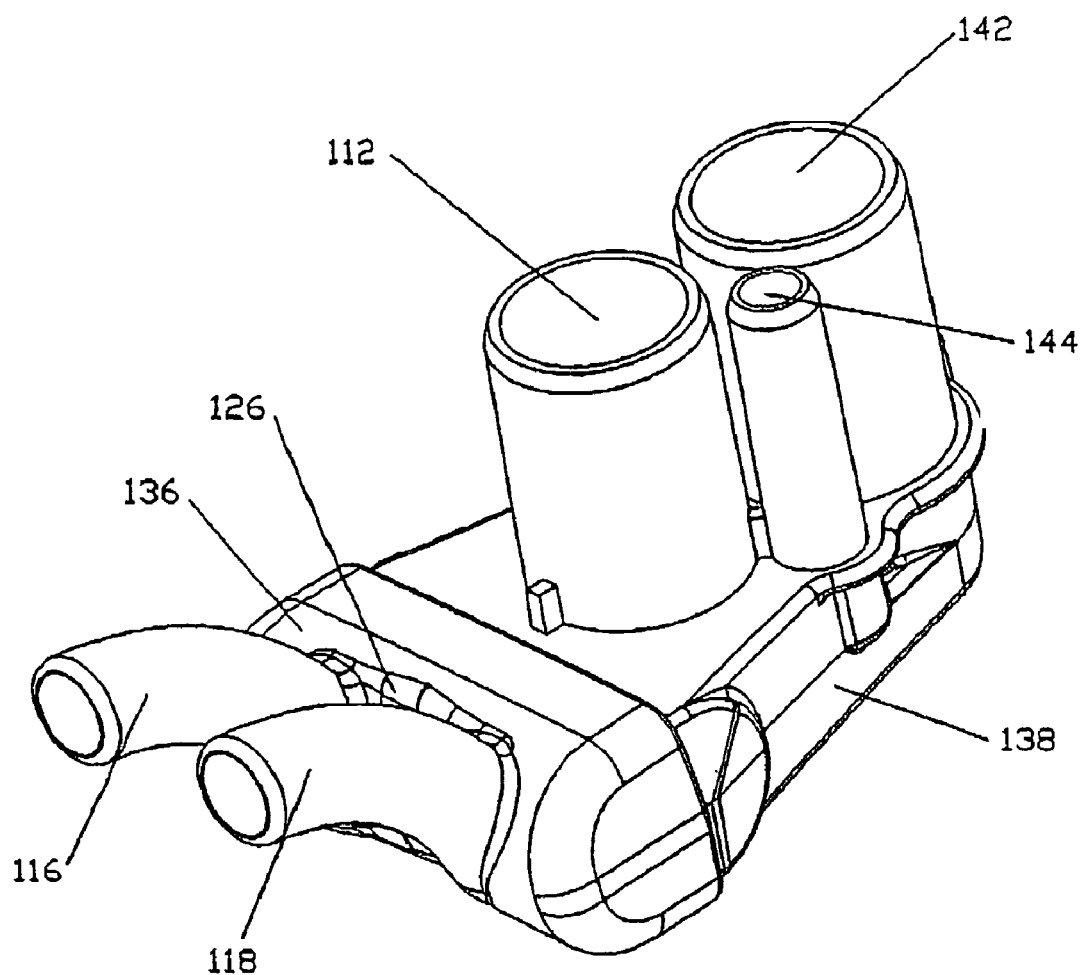
FIG. 6 is a perspective view of the present invention.

An important feature of the present invention is shown in FIG. 4 The two nasal prongs 116, 118 are spaced apart at a distance optimised for the nare spacing for a neonatal infant. However the present invention would be equally applicable for patients of all sizes and the design is easily scalable. It will be appreciated that while the nasal structure of each infant will be somewhat different, almost inevitably the septum will be lower than the fleshy parts on the side of the nose. As mentioned in the discussion of the prior art this may result in irritation and pressure necrosis on the septum. To avoid this, there is a notch 126 or indentation between the two nasal prongs 116, 118 as shown in FIG. 4 and FIG. 6. The indentation 126 is designed such that there will be no contact with the septum.

Reference is now made to FIG. 5 which shows a sectional view of the cannula 100. The inlet manifold 110 is separated from the outlet manifold 130 by a partition 132 running horizontally between the inlet 110 and outlet 130. The partition 132 terminates approximate to the base 134 of the prongs 116, 118. In this fashion there will always be at least some flow flowing directly from the inlet manifold 110 to the outlet manifold 130 as shown by arrow 170. As the diameter of inlet manifold 110 is as large as possible and the entrance/exit of the inlet and outlet manifolds 110, 130 are located each of the partition 132, a path exists from the inlet manifold 110 to the outlet manifold 130 that is a low resistance path shown by arrow 170. This ensures that the dead space or tidal volume is limited to the volume of the prongs 116,118. This configuration results in the minimum build up of expired $CO_2$ and also reduces any opportunity for condensation in the cannula 100.

Figure 7:
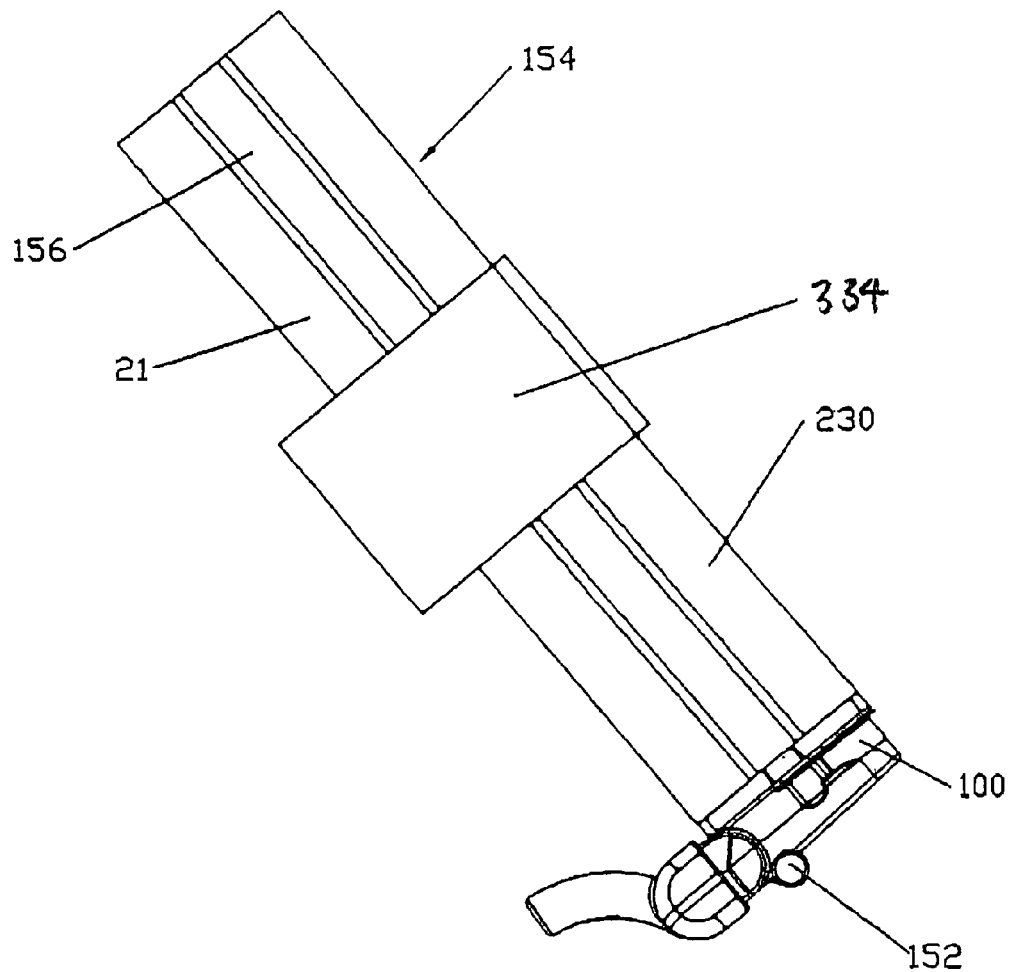
FIG. 7 is a side view of the present invention.

The prongs 116, 118 are formed as part of a moulded rubber or silicon insert 136 which seals to the hard plastic body 138 of the cannula 100 via an interference or compression fit to the hard plastic body 138 of the cannula 100. The prongs 116, 118 are able to be used as a disposable component, or alternatively they can be easily interchanged for a different size, a nasal mask, mouthpiece or other interface as desired. The inlet port 112 is formed as part of the body 138, with inlet 110 at the base of the inlet port 112. Inlet port 112 may be adopted to fit any typical connection configuration for commercially available conduits. Similarly the outlet port 142 is in fluid communication with the outlet manifold 130. A further sensor port 144 can be provided to measure any parameters of the delivered gases for example pressure, temperature, or humidity. As shown in FIG. 7, an inlet/outlet connector 154 can be connected to act as an interface between the nasal cannula 100 and the inhalatory conduit 21 and exhalatory conduit 230. The connector 154 can be formed from extruded PVC or Silicon or any other suitable material. The sensor port 144 can also be connected to a measurement tube 156 which can be formed as part of the connector 154.

Head Securement

Figure 10:
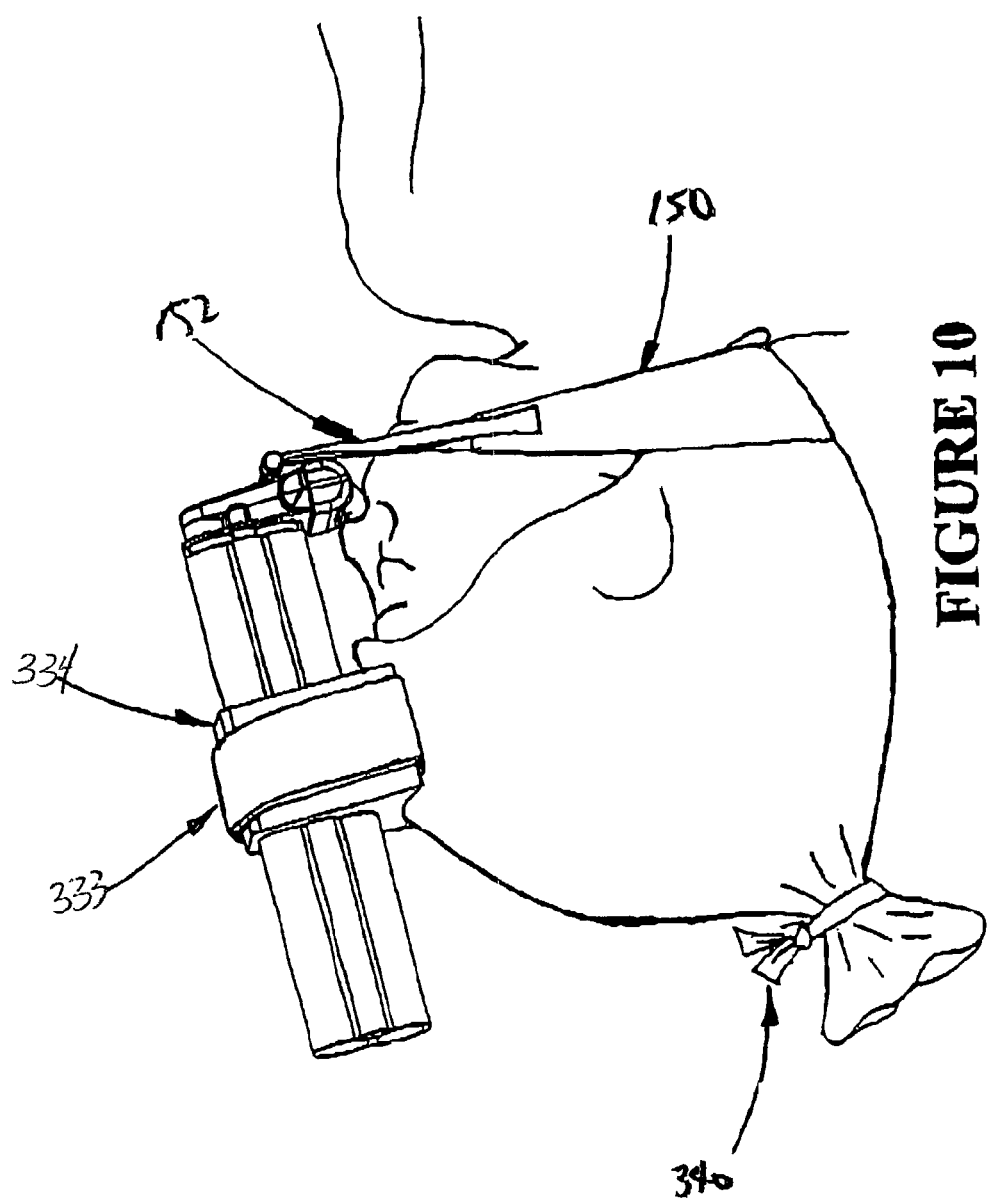
FIG. 10 is an illustration of the present invention is use on a neonate.
Figure 12:
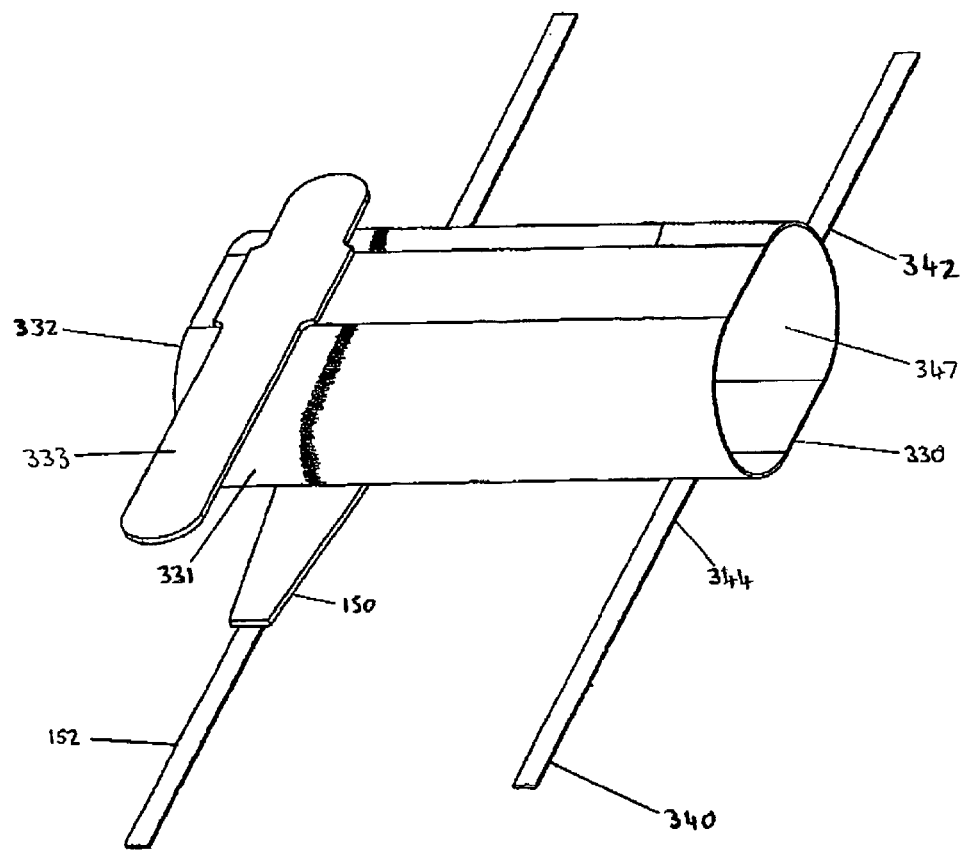
FIG. 12 is a side view of a bonnet, used to hold the cannula of the present invention in position.

As can be seen in FIGS. 10 to 12 the cannula 100 can be secured to the head of a patient 19 by a bonnet. A preferred form of infant bonnet includes a head covering portion 330 which is preferably formed of a stretchable or elastic material having thermal insulation properties. An example of appropriate material is a synthetic or cotton knit fabric. The head covering 330 is provided in the form of a open ended tube. Where the material used for the covering 330 provides more stretch along one principal axis, then that principal axis is preferably aligned across the longitudinal axis of the tube.

As shown in FIG. 12, the head covering 330 has one open end 332. A zone 331 adjacent to this open end 332 stiffer than the surrounding region. The zone 331 may comprise thr example a region of modified knit form, a cuff formed from an alternate material or material configuration or a multi layer hem of the tube.

A strap is provided on the outer surface of the covering 330 for supporting a breathing tube or other medical conduits or wiring.

Figure 1:
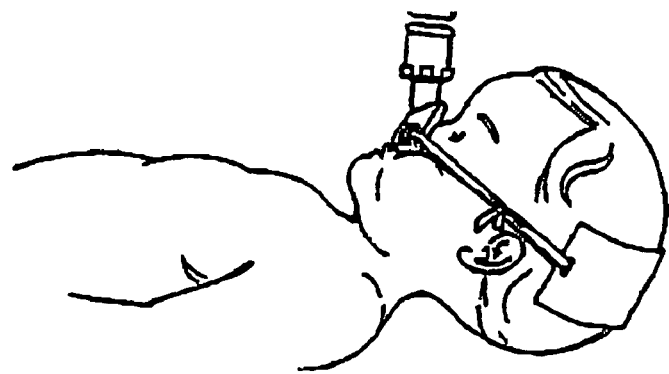
FIG. 1 is a side view of a prior art cannula on an infant.
Figure 2:
FIG. 2 is a perspective view of a prior art cannula on an infant.
Figure 3:
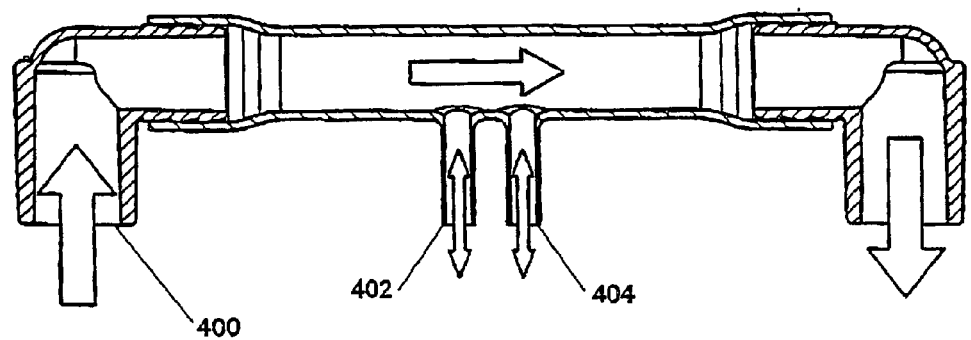
FIG. 3 is a cross section of a prior art cannula.
Figure 13:
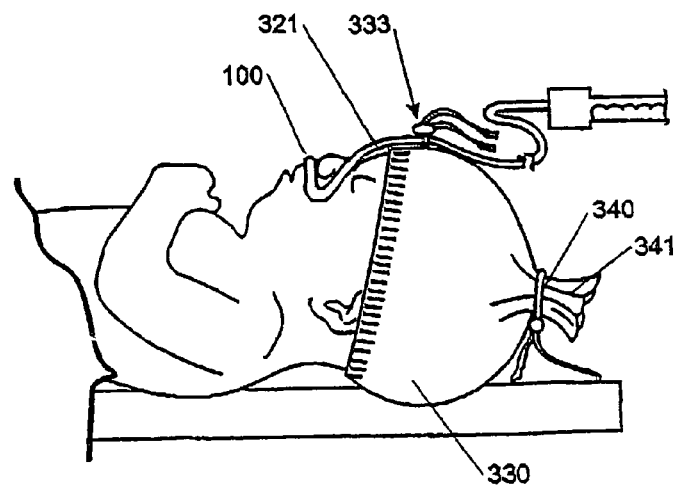
FIG. 13 is an illustration of the bonnet of FIG. 13 in use on an neonate.

The securing means is a strap 333 with which is sewn onto the bonnet. The strap has Velcro® attached at one end. As shown in FIG. 10, a foam block 334 with a triangular outside shape, is fitted over the connector 154. The foam block 334 is positioned on the strap 333. The strap 333 is then closed around the foam block and secured with the Velcro® The foam block 334 is used to firmly hold the connector 154 in place on the bonnet 330 to prevent displacement of the nasal prongs from the nares. Alternatively, as shown in FIG. 13, if inlet/outlet connector 154 is not used, flexible tubes 321 can be attached directly to the head covering 330.

The second open end 347 of the head coveting 330 is preferably formed with a simple hem. The open end 347 is preferably closeable or retainable in a closed position by a closing means 340. The closing means 340 may comprise a further lace or tie of similar configuration to the securing means 333. The lace or tie 340 has two arms 342, 344. The arms 342, 344 preferably tie together or pass through a toggle.

In use the end 347 of head covering 330 is bunched together as an end bunch 341. The loop of lace or tie 340 is passed over the bunch 341. The bunch 341 is firmly secured in a closed configuration within the tightened loop of the lace or tie 340.

The closing means 340 thus provides for easy and efficient closing or opening of the infant bonnet should there be a need for access to the top of the head of the infant. Access may for example be required for placement of electrodes or for cranial ultrasounds. Where access is required the closing means 340 may be released and the bunched portion of end 347 opened to provide necessary access. This access is available without disturbing the other end 332 of the head covering 330 or the securing means 333 supporting medical tubes or wires in place.

Cannula Securement

Ideally the patient 19 should not be mouth breathing. Both inhalation and exhalation should be done through the cannula. In the preferred embodiment the jaw of the patient 19 is held closed to eliminate mouth leak. Mouth leak is undesirable because it causes a lower pressure thus reducing the level of CPAP.

Figure 8:
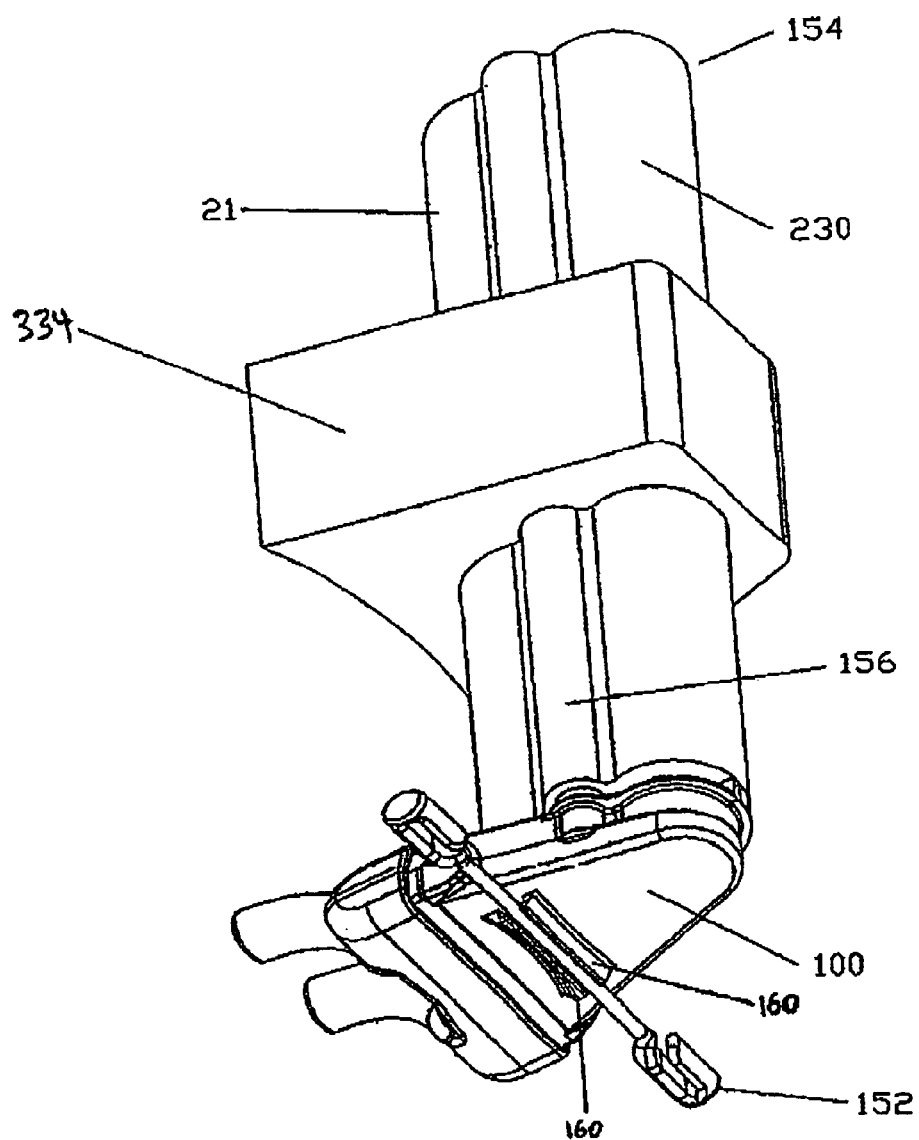
FIG. 8 is a view or the present invention from below.
Figure 9:
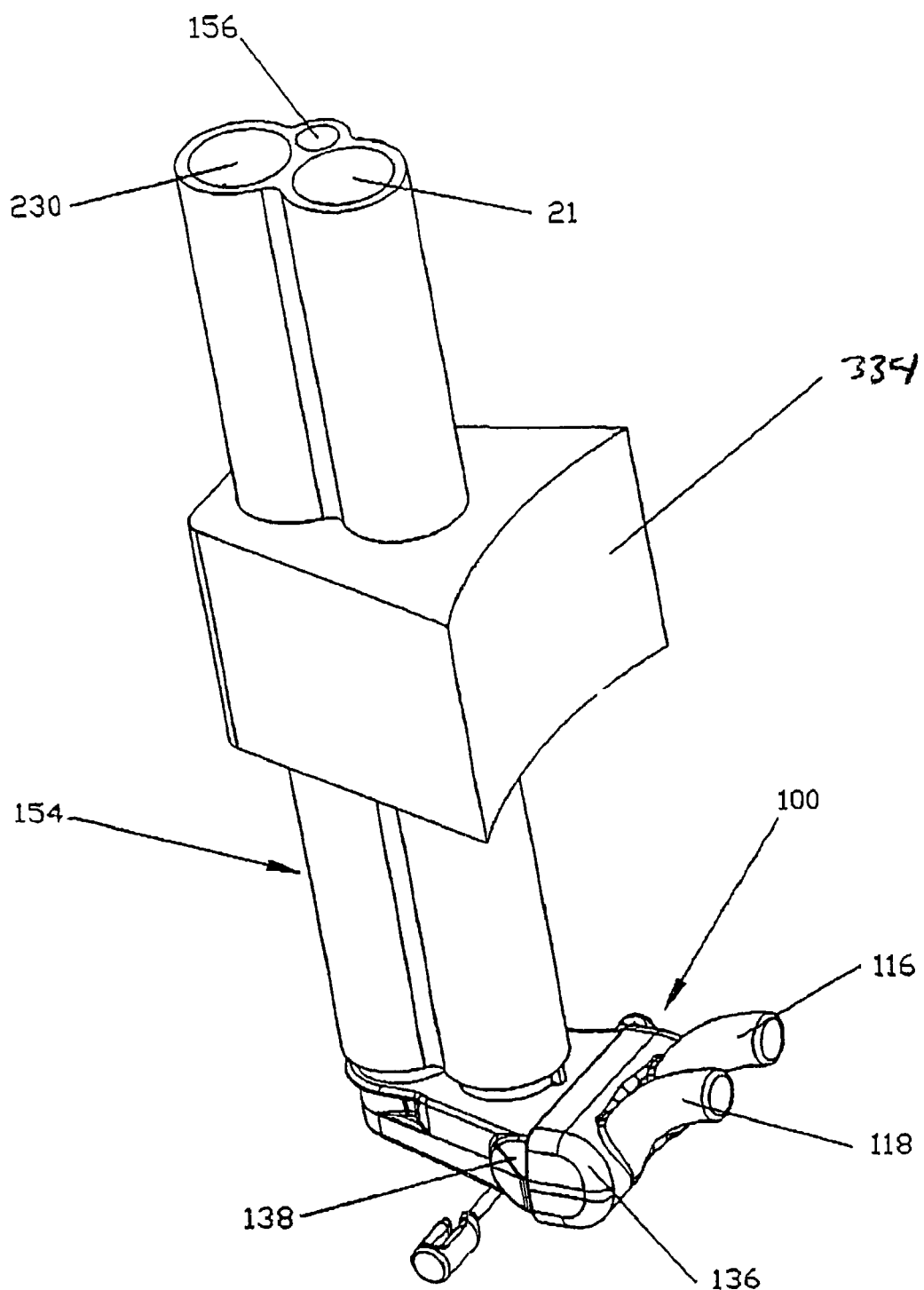
FIG. 9 is a view of the present invention from above.

Referring now particularly to FIGS. 8 to 10 we see that the base of the cannula 100 is secured to the head of the patient 19 using strap 150. Strap 150 passes around the back of the neck of the patient 19 and is connected to the cannula 100 by way of a sliding rod 152. Rod 152 is secured to body 138 by jaws, or clip 160 as shown in FIG. 8. This allows the rod 152 substantial relative lateral and rotational movement with respect to the cannula 100 as the patient 19 twists their head, and exerts forces on the strap 150. Adequate restraining force is provided directly on the cannula 100 without any twisting of the cannula 100. The rod 152 can be a plastic, for example acetal material, engaging into the jaw or clip 160 on the underside of the body 138. The tension in the strap 150 can be adjusted to a comfortable level for the patient 19.

What has been described is an improved nasal cannula of pressure necrosis or irritation that might normally be associated with the use of such a device. The improvement ensures a balanced feed to both prongs, low dead space high flow through the manifold so rebreathing of $CO_2$ is minimised.

The invention claimed is:

1. A nasal cannula for delivering respiratory gases to a patient's nares comprising:
   a gases inlet configured to engage an inspiratory conduit;
   a separate gases outlet configured to engage a separate expiratory conduit,
   a hollow manifold chamber, said gases inlet and said gases outlet in fluid communication through said manifold chamber,
   a pair of nasal prongs in fluid communication with said gases inlet and said gases outlet through said hollow manifold chamber,
   said hollow manifold chamber configured internally to limit the deadspace of said nasal cannula substantially to the volume of said prongs and further configured internally to provide a low resistance path between said gases inlet and said gases outlet such that in use a portion of said respiratory gas flows continuously directly from said gases inlet to said gases outlet, said prongs juxtaposed directly in said low resistance path,
   each of said prongs spaced equidistant from said gases inlet such that said respiratory gas is available to each of said prongs simultaneously, and
   each of said prongs spaced equidistant from said gases outlet such that the potential for rebreathing expired gases is reduced.

2. A nasal cannula as claimed in claim 1 wherein said nasal cannula further has rod and a clip engagement for securing said cannula to a strap, said rod and clip arrangement comprising:
   a cylindrical rod with two end connectors at or proximate each end, said connectors configured to receive a portion of said strap and to hold said strap relative to the rod, and
   a clip connected to the cannula, said clip having at least two projecting members spaced to receive a segment of said rod and retain said clip in contact with said rod in such a manner that said rod is able to slide laterally and rotate about a longitudinal axis relative to said clip when engaged.

3. A nasal cannula as claimed in claim 2 wherein said strap includes an adjustable attachment to said rod.

4. A nasal cannula as claimed in claim 3 wherein said securement has a head covering bonnet adapted to at least partially cover the head of said patient, said bonnet having an elastic cuff to securely locate said bonnet on said patient head, and a securing strap for use in holding at least one of said inspiratory conduit or said expiratory conduit in a position on said bonnet against at least lateral movement, said securing strap connected with said bonnet on the outer surface thereof.

5. A nasal cannula as claimed in claim 4 wherein said bonnet is formed of a knit fabric in a tubular configuration, open at both ends, said securing strap is connected with said outer surface adjacent one of said ends, with an end closure mechanism connected with said outer surface adjacent the other of said ends, said end closure mechanism operable to hold the said knit fabric at said end in a closed, bunched together, condition.

6. A nasal cannula as claimed in claim 5 wherein said end closure mechanism is a lace or tie stitched to said cover.

7. A nasal cannula as claimed in claim 6 wherein said lace or tie is centrally secured to said cover to provide two arms, and said end closure mechanism further comprises a tightening toggle through which said arms pass, said tightening toggle slidable on said arms, said tightening toggle operable between at least two conditions, being biased to a pinch off condition in which said arms of said lace or tie are clamped within said toggle, said toggle manipulable to a free configuration in which said toggle may slide along said arms of said lace or tie.

8. A nasal cannula as claimed in claim 1 wherein said cannula also has a strap and a head securement,
   said strap passing around the back of said patient's neck and engaging with said cannula below said prongs to form a strap engagement, and
   said head securement located above said prongs and configured to engage at least one of said inspiratory conduit, or said expiratory conduit, or both and hold said conduit or conduits in position on said patient's head,
   said strap engagement and said head securement securing said cannula in place on said patient.

9. A nasal cannula as claimed in claim 8 wherein said strap engagement and said head securement secure said cannula in place on said patient in such a manner that contact between said cannula and said patient occurs only at the patient's nares, except for said strap engagement and said head securement.

10. A nasal cannula as claimed in claim 1 wherein said manifold chamber is partially bisected by a partition, said partition creating a tortuous pathway for gases flowing through said manifold chamber between said inlet port and said outlet port, said nasal prongs juxtaposed in said tortuous pathway.

* * * * *

UNITED STATES PATENT AND TRADEMARK OFFICE
CERTIFICATE OF CORRECTION

| | | |
|---|---|---|
| PATENT NO. | : 7,905,232 B2 | Page 1 of 1 |
| APPLICATION NO. | : 10/242903 | |
| DATED | : March 15, 2011 | |
| INVENTOR(S) | : Olsen et al. | |

It is certified that error appears in the above-identified patent and that said Letters Patent is hereby corrected as shown below:

On Page 1 (item 56), Column 2, Under Foreign Patent Documents, please add
--AU 156493 01/24/52--.

In Column 3, Line 60, change "or" to --of--.

In Column 4, Line 9, change "(CRAP)" to --(CPAP)--.

In Column 5, Line 27, change "each" to --each side--.

In Column 6, Line 1, change "thr" to --for--.

In Column 6, Line 20, change "coveting" to --covering--.

Signed and Sealed this
Third Day of January, 2012

David J. Kappos
*Director of the United States Patent and Trademark Office*